United States Patent

Urella et al.

[11] Patent Number: 5,138,722
[45] Date of Patent: Aug. 18, 1992

[54] HEADSET EAR SEAL

[75] Inventors: Richard M. Urella, Shrewsbury; William B. Van Lennep, Pepperell, both of Mass.

[73] Assignee: David Clark Company Inc., Worcester, Mass.

[21] Appl. No.: 724,674

[22] Filed: Jul. 2, 1991

[51] Int. Cl.⁵ .............................................. A42B 1/06
[52] U.S. Cl. ........................................... 2/209; 2/413
[58] Field of Search ................... 2/2, 171, 208, 209, 2/410, 411, 412, 413, 414, 416, 423

[56] References Cited

U.S. PATENT DOCUMENTS

| | | | |
|---|---|---|---|
| 2,989,598 | 6/1961 | Touger et al. | 179/182 |
| 2,990,553 | 7/1961 | Ulrich et al. | 2/209 |
| 3,051,961 | 9/1962 | Clark | 2/209 |
| 3,052,887 | 9/1962 | Sockel et al. | 2/9 |
| 3,073,410 | 1/1963 | Gongoll et al. | 181/23 |
| 3,571,813 | 3/1971 | Allen | 2/209 |
| 3,593,341 | 7/1971 | Aileo | 2/209 |
| 3,862,451 | 1/1975 | Miller et al. | 2/209 |
| 3,908,200 | 9/1975 | Lundin | 2/209 |
| 4,456,642 | 6/1984 | Burgdorfer et al. | 428/68 |
| 4,471,496 | 9/1984 | Gardner | 2/209 |
| 4,572,323 | 2/1986 | Randall | 181/129 |
| 4,674,134 | 6/1987 | Lundin | 2/209 |
| 4,856,118 | 8/1989 | Sapiejewski | 2/209 |
| 4,905,322 | 3/1990 | Aileo et al. | 2/209 |
| 4,944,361 | 7/1990 | Lindgren et al. | 181/129 |
| 4,958,697 | 9/1990 | Moody | 181/129 |
| 4,989,271 | 2/1991 | Sapiejewski | 2/209 |
| 5,003,631 | 4/1991 | Richardson | 2/413 |
| 5,020,163 | 6/1991 | Aileo | 2/209 |
| 5,023,955 | 6/1991 | Murphy | 2/209 |

Primary Examiner—Werner H. Schroeder
Assistant Examiner—Diana L. Biefeld
Attorney, Agent, or Firm—Samuels, Gauthier & Stevens

[57] ABSTRACT

An ear seal for use with an earcup of a headset. The ear seal includes at least one ring of noise attenuating material, the material being a mixture of a dilatant silicone compound and a silicone fluid. A sheath is provided to enclose the ring of noise attenuating material. A ring of soft compliant material may also be used adjacent the ring of noise attenuating material for added comfort to the user. A sheath may be provided to enclose both the ring of soft compliant material and the ring of noise attenuating material.

18 Claims, 2 Drawing Sheets

A - DIELECTRIC GEL OVER DILATANT SILICONE COMPOUND
B = DIELECTRIC GEL OVER SLOW RECOVERY FOAM
C = GLYCERIN OVER SLOW RECOVERY FOAM

HEADSET EAR SEAL

BACKGROUND OF THE INVENTION

The invention relates to ear seals for use in noise attenuating headsets and other like headgear incorporating ear protectors designed to reduce noise levels.

Circumaural hearing protectors function by enclosing the ears of a user within earcups, typically plastic domes. Conformable ear seals are interposed between the earcups and the user's head to assist in isolating the ears from offending noise originating outside the earcups. The earcups are typically attached to a spring and suspension assembly which applies a force urging the ear seals in place against the head of the user.

Various problems exist which limit the effectiveness of circumaural hearing protectors. The noise attenuation achievable by hearing protectors at low frequencies is extremely limited due to undesirable vibration of the dome and ear seal assemblies induced by external noise. Also, leakage occurring between the head of the user and the ear seals provides a direct path for the entry of external noise. At lower frequencies below about 1 kHz, bone conduction of vibrations further limits achievable noise attenuation. In addition, vibrations may be transmitted along the surface of the flesh of the user under the ear seals so as to penetrate the earcup.

The prior art includes ear seals which attempt to address the above mentioned problems in hearing protectors. For example, Lundin U.S. Pat. No. 4,674,134, entitled "Ear Muff Having Sealing Ring Including Liquid and Foam Plastic Layers", describes a sealing ring having a liquid layer enclosed in a sheath overlying a foamed plastic layer. The ear seal includes an inner sheath which encloses the liquid layer, and an outer sheath which encloses both the inner sheath with the liquid layer and the foamed plastic layer. Sapiejewski U.S. Pat. No. 4,856,118, entitled "Head Phone Cushioning", describes a head phone cushion having two concentric rings of non-liquid silicone gel on a layer of soft, slow recovery foam enclosed in a thin stretchable layer of polyurethane skin.

Noise attenuation and comfort are qualities which are normally in conflict with one another in circumaural hearing protector systems. High attenuation has typically dictated the use of stiff, non-springy ear seal materials which because of their nonconforming nature, require excessive head band clamping force to insure a good acoustic seal against the head of the user. The result is often an ear seal that provides good attenuation at the expense of user comfort.

Soft ear seals with larger geometry and low head band clamping force provide comfort to the user, but allow the transmission of vibrations, reduced damping, and lower attenuation. The low clamping force increases the likelihood of leaks at the interface between the ear seal and the head of the user.

It is therefore an object of the present invention to provide an ear seal that offers superior attenuation as well as a high degree of comfort.

SUMMARY OF THE INVENTION

According to one aspect of the present invention, there is provided an ear seal for use in an earcup of a head set. The ear seal comprises at least one ring of noise attenuating material enclosed within a flexible sheath, the noise attenuating material comprising a mixture of a dilatant silicone compound and a silicone fluid.

In another aspect of the present invention, there is provided at least one ring of a soft compliant material which is disposed adjacent to the at least one ring of noise attenuating material, with a sheath enclosing the at least one ring of soft compliant material and the at least one ring of noise attenuating material.

BRIEF DESCRIPTION OF THE DRAWINGS

The present invention is pointed out with particularity in the appended claims. The above and further objectives and advantages of this invention may be better understood by referring to the following description taken in conjunction with the accompanying drawings in which:

DESCRIPTION OF THE ILLUSTRATED EMBODIMENTS

Figure 1:
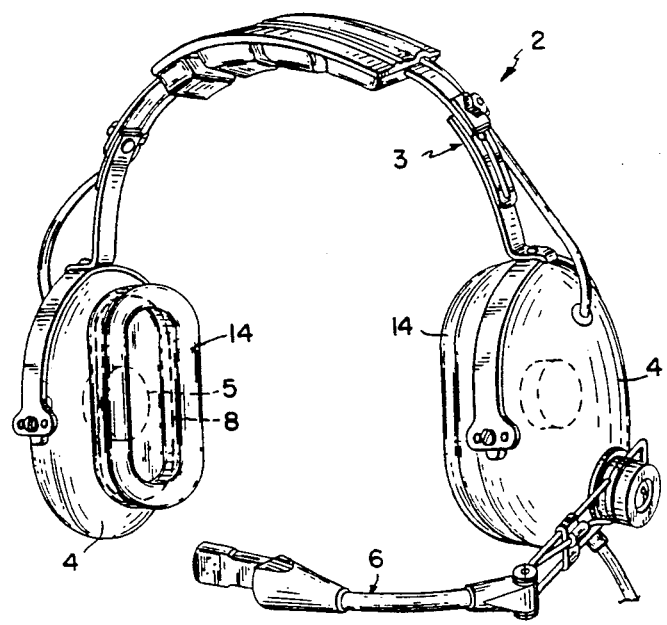
FIG. 1 is a perspective view of a headset in accordance with the present invention.

FIG. 1 illustrates a noise attenuating headset 2 in accordance with the present invention. The headset includes earcups 4 which are attached to a spring and suspension assembly 3. Speakers 5 and microphone boom assembly 6 are provided for communication capabilities. Each of the earcups further include earseals 10 which are attached to lip portions 8 associated with the earcups.

Figure 2:
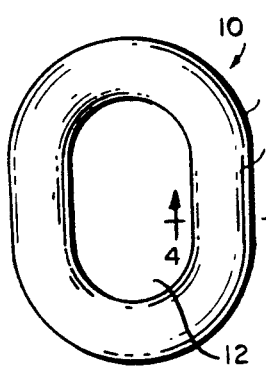
FIG. 2 is a top plan view of an ear seal in accordance with the present invention.
Figure 3:
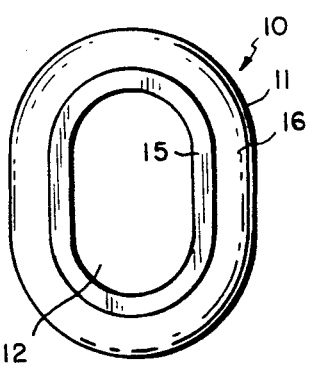
FIG. 3 is a bottom plan view of an ear seal in accordance with the present invention.

With reference to FIG. 2 and FIG. 3, an ear seal 10 in accordance with the present invention is shown. The ear seal 10 includes a thin flexible ring-shaped sheath 11 having an upper portion 14 and a lower portion 15. The sheath is typically formed from polyurethane or the like, and surrounds an opening 12 through which sound passes from the speaker 5 contained within the earcup 4 to the ear of the user. The bottom portion 15 is formed integrally with concentric ring-shaped flap portion 16. The flap portion is also made from a thin resilient skin such as polyurethane, and provides a means of attaching the ear seal to the aforesaid earcup. Conventional earcups typically include the lip portions 8 around which the bottom portion 15 and the flap portion 16 tightly fit.

Figure 4:
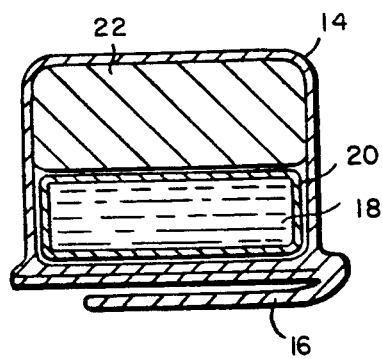
FIG. 4 is a cross-sectional view of an ear seal in accordance with the present invention taken along line 4—4 of FIG. 2.

Referring now to FIG. 4, a ring of noise attenuating material 18 is enclosed within the sheath 11. The noise attenuating material is preferably a mixture of a dilatant silicone compound and a silicone oil. The term dilatant herein meaning having the characteristics of increasing in viscosity and setting to a solid as a result of deformation by expansion, pressure, or agitation. One such dilatant silicone compound, is Dow Corning ® 3179 dilatant compound. Furthermore, one such silicone fluid is Dow Corning ® Q13563. The noise attenuating material 18 possesses qualities of compliance and softness providing comfort over a wide temperature range from approximately 40° F. to 175° F. More importantly, this particular material has unexpectedly provided an excellent medium for the isolation and damping of vibrations.

An inner sheath 20 of a thin flexible skin such as polyurethane is provided to enclose the ring of noise attenuating material 18 so as to isolate same within the enclosure of the sheath 11.

A ring of soft compliant material 22 such as a dielectric silicone gel is disposed within the sheath 11 adjacent to the ring of noise attenuating material 18. It is preferred that the ring of soft compliant material 22 be disposed to overlie the ring of noise attenuating material 18 so as to be nearer to the head of the user of the ear seal for additional comfort.

Figure 5:
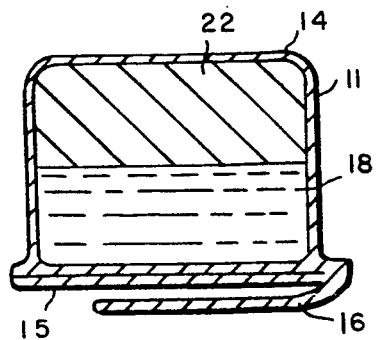
FIG. 5 is a cross-sectional view of an alternate embodiment of an ear seal in accordance with the present invention taken along line 4—4 of FIG. 2.
Figure 6:
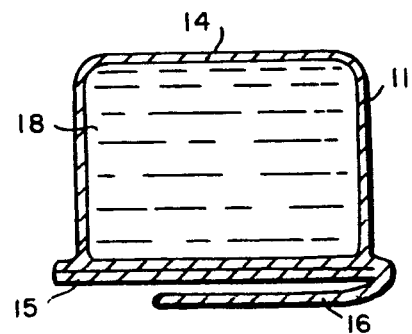
FIG. 6 is a cross-sectional view of another alternate embodiment of an ear seal in accordance with the present invention taken along line 4—4 of FIG. 2.

It will be appreciated by those skilled in the art that modifications to the present invention may include the use of the noise attenuating material 18 and the soft compliant material 22 enclosed within the sheath 11 without the inner sheath 20 separating the materials as shown in FIG. 5. Furthermore, the ear seal 10 in accordance with the present invention may be configured to include only the ring of noise attenuating material 18 enclosed within the sheath 11 as shown in FIG. 6.

Figure 7:
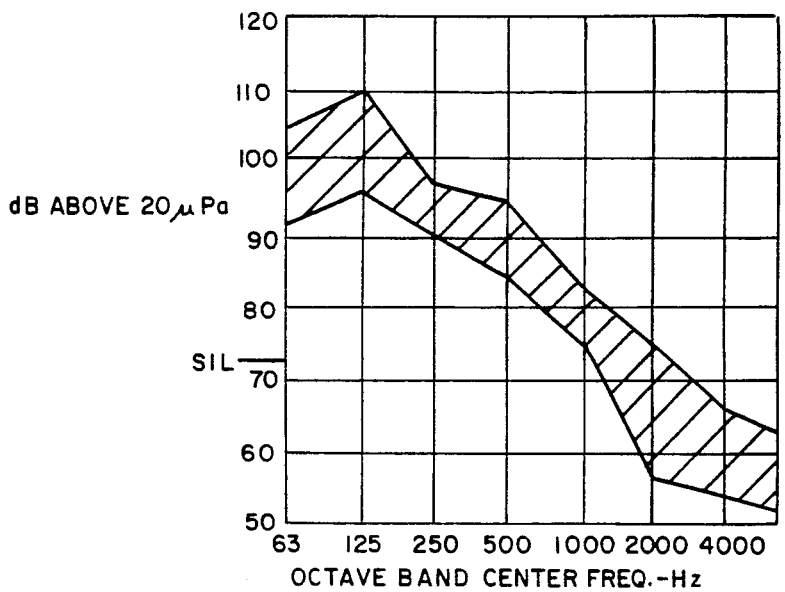
FIG. 7 is a graph of typical measured noise level in the cockpit of single engine piston driven aircraft.
Figure 8:
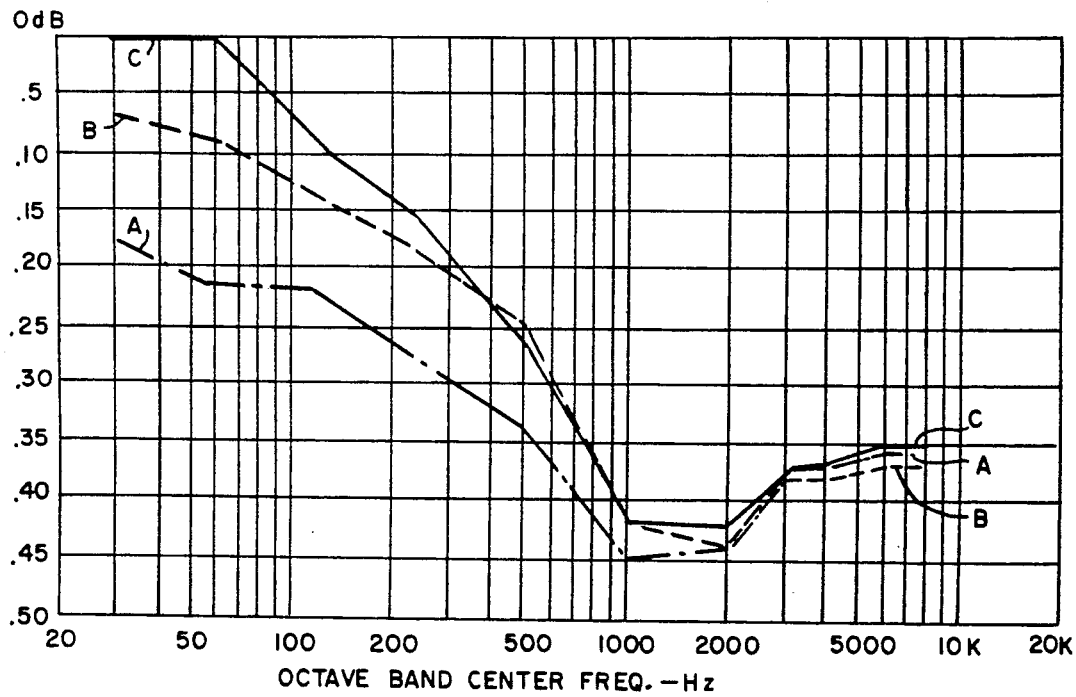
FIG. 8 is a graph comparing the noise attenuation capability of an ear seal in accordance with the present invention with those of ear seals of the prior art.

The superior noise attenuation characteristics of the ear seal of the present invention can best be appreciated by further reference to FIGS. 7 and 8.

FIG. 7 illustrates a graph of measured noise levels in the cockpit of a general aviation single engine piston driven aircraft. This graph appeared originally in a document entitled "Audio System Characteristics and Minimum Performance Standards Aircraft Microphones (except carbon), Aircraft Head Sets and Speakers Air Craft Audio Selector Panels and Amplifiers", Radio Technical Commission for Aeronautics, Jan. 25, 1980, prepared by RTCA SC-132 (RTCA/DO-170). The plot shows data representative of noise measured in eight aircraft types with plot coordinates dB above 20 μPa verses octave band center frequency in Hertz. It will be appreciated that greater noise problems exist in the lower octave band center frequency range, approximately 63-1000 Hz. Tests were done comparing attenuation (−dB) of the ear seal in accordance with the present invention (A) utilizing both the dielectric gel and the noise attenuating material of dilatant silicone compound mixed with silicone fluid to prior art ear seals, one using glycerin and slow recovery foam (B) and the other using dielectric gel and slow recovery foam (C), the following results were achieved:

| Octave Band Center Frequency ($H_z$) | Ear Seal Attenuation (−dB) Comparison* | | |
|---|---|---|---|
| | (A) Dielectric Gel + Dilatant Compound | (B) Dielectric Gel + Slow Recovery Foam | (C) Glycerin + Slow Recovery Foam |
| 31 | 18 | 7 | 0 |
| 62 | 22 | 9 | 0 |
| 125 | 22 | 14 | 9 |
| 250 | 28 | 18 | 16 |
| 500 | 33 | 25 | 26 |
| 1000 | 45 | 42 | 42 |
| 2000 | 44 | 43 | 44 |
| 3150 | 37 | 38 | 37 |

| Octave Band Center Frequency ($H_z$) | Ear Seal Attenuation (−dB) Comparison* -continued | | |
|---|---|---|---|
| | (A) Dielectric Gel + Dilatant Compound | (B) Dielectric Gel + Slow Recovery Foam | (C) Glycerin + Slow Recovery Foam |
| 4000 | 37 | 38 | 37 |
| 6300 | 36 | 37 | 35 |
| 8000 | 36 | 37 | 35 |

*All tests done with David Clark Company, Inc. shallow dome, 2.0 lbs of headband force, flat plate, 50th percentile head width.

FIG. 8 is a graph comparison of the attenuation test between the prior art ear seals and the ear seal in accordance with the present invention. Plot line A corresponds to the data associated with the ear seal according to the present invention utilizing a ring of dielectric gel overlying a ring of noise attenuating material comprising dilatant silicone compound and silicone fluid. Plot lines B and C relate to the data acquired for ear seals utilizing a ring of dielectric gel overlying a ring of slow recovery foam and a ring of glycerin overlying a ring of slow recovery foam respectively.

The noise attenuation of the ear seal in accordance with the present invention over the critical octave band center frequency range (31-1000 Hz) far exceeds the results associated with the prior art ear seals. It will be appreciated by those skilled in the art that a 6 dB difference in attenuation corresponds to a doubling of sound pressure level. Therefore, as an example, with reference to the attenuation levels of the three ear seals A, B, and C shown in FIG. 8 at octave band center frequency 62 Hz, the ear seal in accordance with the present invention (A) attenuates approximately four times the sound pressure level of the prior art ear seal B, and approximately seven times the sound pressure level of the prior art ear seal C. These factors are derived from the attenuation levels corresponding to 62 Hz, wherein the ear seal if the present invention (A) experiences 22 dB attenuation, the prior art seal experiences 9 dB attenuation, and the prior art seal C experiences 0 dB attenuation. Thus, it has been discovered that the use of a ring of dielectric gel overlying a ring of noise attenuating material comprising a dilatant silicone compound and a silicone fluid in an ear seal provides far superior noise attenuation.

Having shown illustrated embodiments, those skilled in the art will realize many variations are possible which will still be within the scope and spirit of the claimed invention. Therefore it is the intention to limit the invention only as indicated by the scope of the claims.

What is claimed is:

1. An ear seal for use in an earcup of a headset, comprising:
    at least one ring of a noise attenuating material, said material comprising a mixture of a dilatant silicone compound and a silicone fluid; and
    a first sheath enclosing said at least one ring of noise attenuating material.

2. The ear seal as claimed in claim 1, wherein said noise attenuating material is a soft compliant material, thus providing an improved acoustic seal and a comfortable fit to a user of said headset.

3. The ear seal as claimed in claim 2, wherein said sheath comprises a thin resilient skin.

4. The ear seal as claimed in claim 3, wherein said skin is polyurethane.

5. The ear seal as claimed in claim 1, further comprising:
- at least one ring of a soft compliant material disposed adjacent to said first sheath which encloses said at least one ring of noise attenuating material; and
- a second sheath enclosing both said first sheath which encloses said at least one ring of noise attenuating material and said at least one ring of soft compliant material.

6. The ear seal as claimed in claim 5, wherein said soft compliant material is a silicone gel.

7. The ear seal as claimed in claim 5, wherein said second sheath comprises a thin resilient skin.

8. The ear seal as claimed in claim 7, wherein said skin is polyurethane.

9. The ear seal as claimed in claim 5, wherein said at least one ring of soft compliant material is disposed atop said first sheath within said second sheath so as to be proximate to the head of a user of said ear seal.

10. An ear seal for use in a earcup of a headset, comprising:
- at least one ring of a noise attenuating material, said material comprising a mixture of a dilatant silicone compound and a silicone fluid;
- at least one ring of a soft compliant material disposed adjacent to said at least one ring of noise attenuating material; and
- a first sheath enclosing said at least one ring of noise attenuating material and said at least one ring of soft compliant material.

11. The ear seal as claimed in claim 10, further comprising a second sheath enclosing said at least one ring of noise attenuating material so as to separate same from said at least one ring of soft compliant material within said first sheath.

12. The ear seal as claimed in claim 11, wherein said second sheath comprises a thin resilient skin.

13. The ear seal as claimed in claim 12, wherein said skin is polyurethane.

14. The ear seal as claimed in claim 10, wherein said soft compliant material is a silicone gel.

15. The ear seal as claimed in claim 10, wherein said at least one ring of soft compliant material is disposed atop said at least one ring of noise attenuating material so as to be proximate to the head of a user of said ear seal.

16. The ear seal as claimed in claim 10, wherein said first sheath comprises a thin resilient skin.

17. The ear seal as claimed in claim 16, wherein said skin is polyurethane.

18. A noise attenuating material for use in an ear seal of a headset, said material comprising a mixture of a dilatant silicone compound and a silicone fluid.

* * * * *